(12) United States Patent
Orbay et al.

(10) Patent No.: US 9,173,691 B2
(45) Date of Patent: Nov. 3, 2015

(54) DEVICES, IMPLEMENTS AND METHODS FOR THE TREATMENT OF A MULTI-AXIS JOINT

(75) Inventors: Jorge L. Orbay, Miami, FL (US);
Thomas H. Norman, Miami, FL (US);
Ronald Litke, Shelton, CT (US)

(73) Assignee: Skeletal Dynamics LLC, Miami, FL (US)

( * ) Notice: Subject to any disclaimer, the term of this patent is extended or adjusted under 35 U.S.C. 154(b) by 756 days.

(21) Appl. No.: 13/114,648

(22) Filed: May 24, 2011

(65) Prior Publication Data

US 2011/0288550 A1    Nov. 24, 2011

Related U.S. Application Data

(60) Provisional application No. 61/347,517, filed on May 24, 2010, provisional application No. 61/390,420, filed on Oct. 6, 2010.

(51) Int. Cl.
| | |
|---|---|
| *A61F 2/42* | (2006.01) |
| *A61B 17/80* | (2006.01) |
| *A61B 17/15* | (2006.01) |
| A61B 17/84 | (2006.01) |
| A61B 17/88 | (2006.01) |

(Continued)

(52) U.S. Cl.
CPC .............. *A61B 17/808* (2013.01); *A61B 17/152* (2013.01); *A61B 17/8095* (2013.01); *A61F 2/4241* (2013.01); *A61B 17/8085* (2013.01); *A61B 17/842* (2013.01); *A61B 17/8863* (2013.01); *A61F 2/4684* (2013.01); *A61F 2002/30112* (2013.01); *A61F 2002/30253* (2013.01); *A61F 2002/30301* (2013.01); *A61F 2002/30616* (2013.01); *A61F 2002/30688* (2013.01); *A61F 2002/30772* (2013.01); *A61F 2002/30878* (2013.01); *A61F 2002/30884* (2013.01); *A61F 2002/4256* (2013.01); *A61F 2002/4258* (2013.01); *A61F 2310/00029* (2013.01); *A61F 2310/00047* (2013.01); *A61F 2310/00407* (2013.01)

(58) Field of Classification Search
CPC ........... A61F 2/4241; A61F 2002/4256; A61F 2002/4258
USPC .............................................. 623/21.15, 21.18
See application file for complete search history.

(56) References Cited

U.S. PATENT DOCUMENTS

| | | | | |
|---|---|---|---|---|
| 4,194,250 | A | * 3/1980 | Walker | ........................ 623/23.39 |
| 5,405,400 | A | 4/1995 | Linscheid et al. | |
| 5,549,690 | A | 8/1996 | Hollister et al. | |

(Continued)

FOREIGN PATENT DOCUMENTS

| | | |
|---|---|---|
| EP | 0669117 A1 | 8/1995 |
| WO | 9509587 A1 | 4/1995 |

(Continued)

*Primary Examiner* — Randy Shay
(74) *Attorney, Agent, or Firm* — Laurence A. Greenberg; Werner H. Stemer; Ralph E. Locher

(57) ABSTRACT

A system, devices and methods for performing an osteotomy on a bone of a multi-axis joint are provided. A cutting guide system is provided for performing one or more cuts to the bone, using the articular surfaces of the articulating bones as a reference. If desired, a prosthesis can be used to emulate the osteotomy and substitute for a damaged articular surface of a bone of a multiaxis joint.

13 Claims, 11 Drawing Sheets

(51) Int. Cl.
   *A61F 2/46*  (2006.01)
   *A61F 2/30*  (2006.01)

(56) References Cited

U.S. PATENT DOCUMENTS

| 5,645,605 | A | 7/1997 | Klawitter |
| 6,159,247 | A | 12/2000 | Klawitter et al. |
| 7,182,787 | B2 | 2/2007 | Hassler et al. |
| 7,641,696 | B2 | 1/2010 | Ogilvie et al. |
| 2002/0065561 | A1 | 5/2002 | Ogilvie et al. |
| 2004/0193164 | A1 | 9/2004 | Orbay |
| 2004/0260301 | A1 | 12/2004 | Lionberger et al. |
| 2005/0033426 | A1* | 2/2005 | Ogilvie et al. ............. 623/16.11 |
| 2005/0119757 | A1* | 6/2005 | Hassler et al. ............. 623/21.15 |
| 2005/0251265 | A1* | 11/2005 | Calandruccio et al. .... 623/21.15 |
| 2009/0276052 | A1* | 11/2009 | Regala et al. ............. 623/18.11 |
| 2010/0057215 | A1* | 3/2010 | Graham ..................... 623/21.15 |

FOREIGN PATENT DOCUMENTS

| WO | 9819637 | A1 | 5/1998 |
| WO | 2010033691 | A2 | 3/2010 |

* cited by examiner

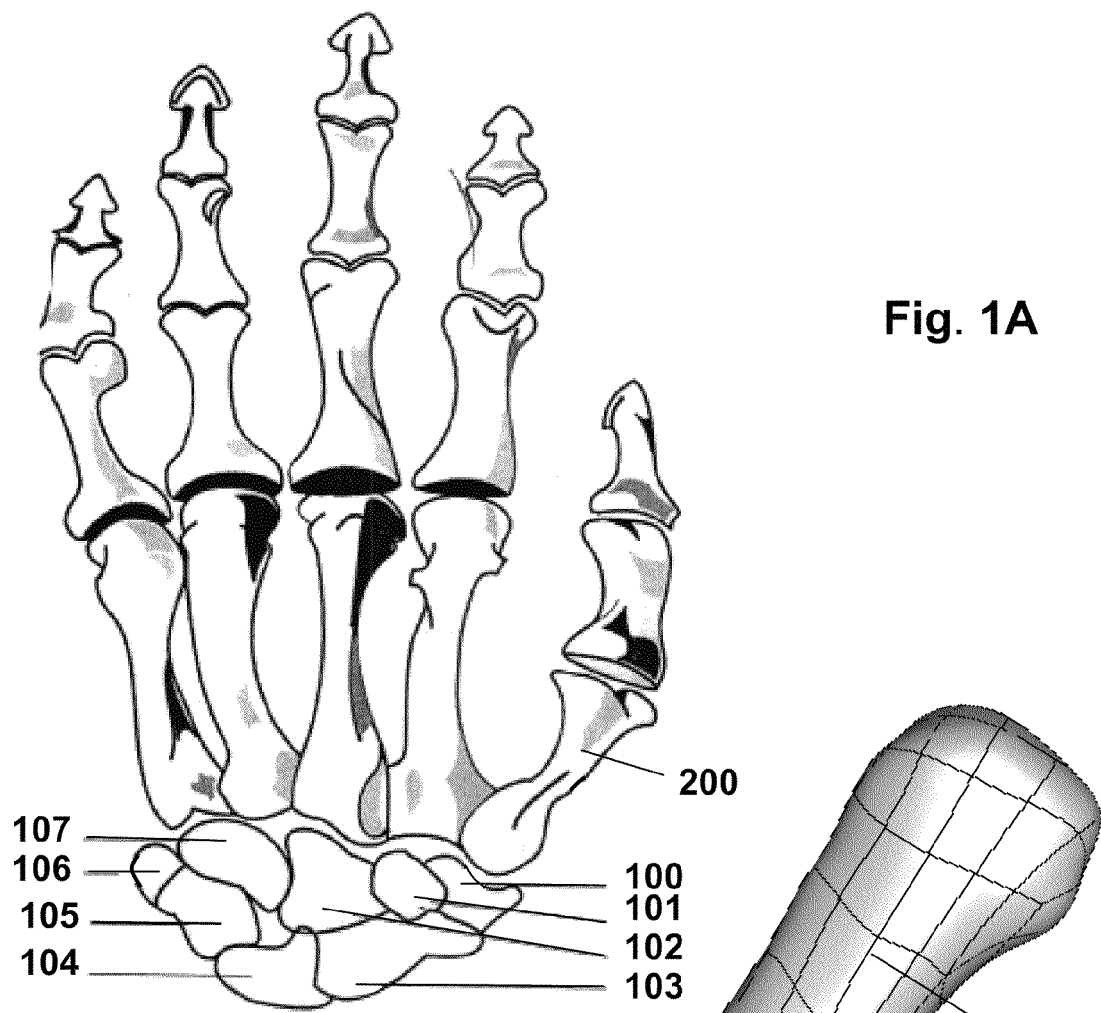
Fig. 1A
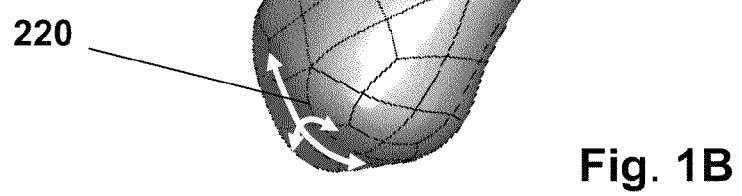
Fig. 1B
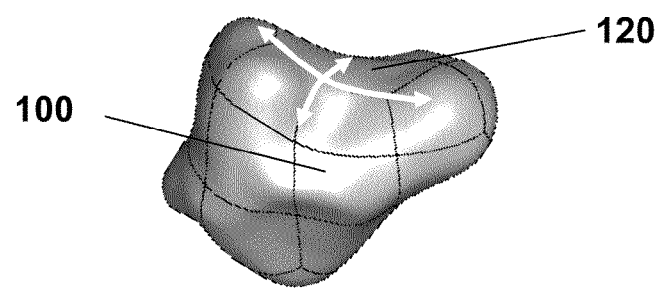

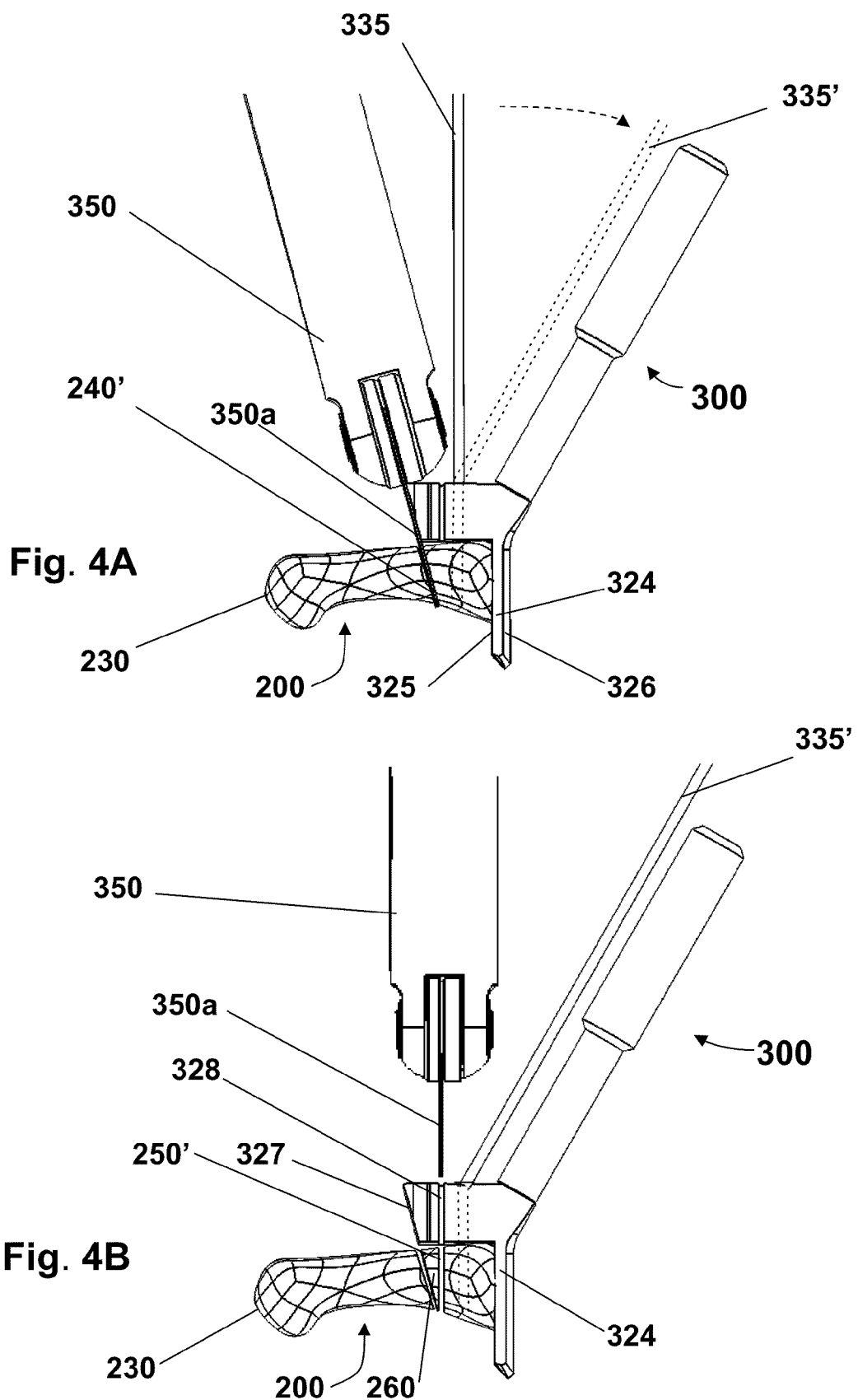

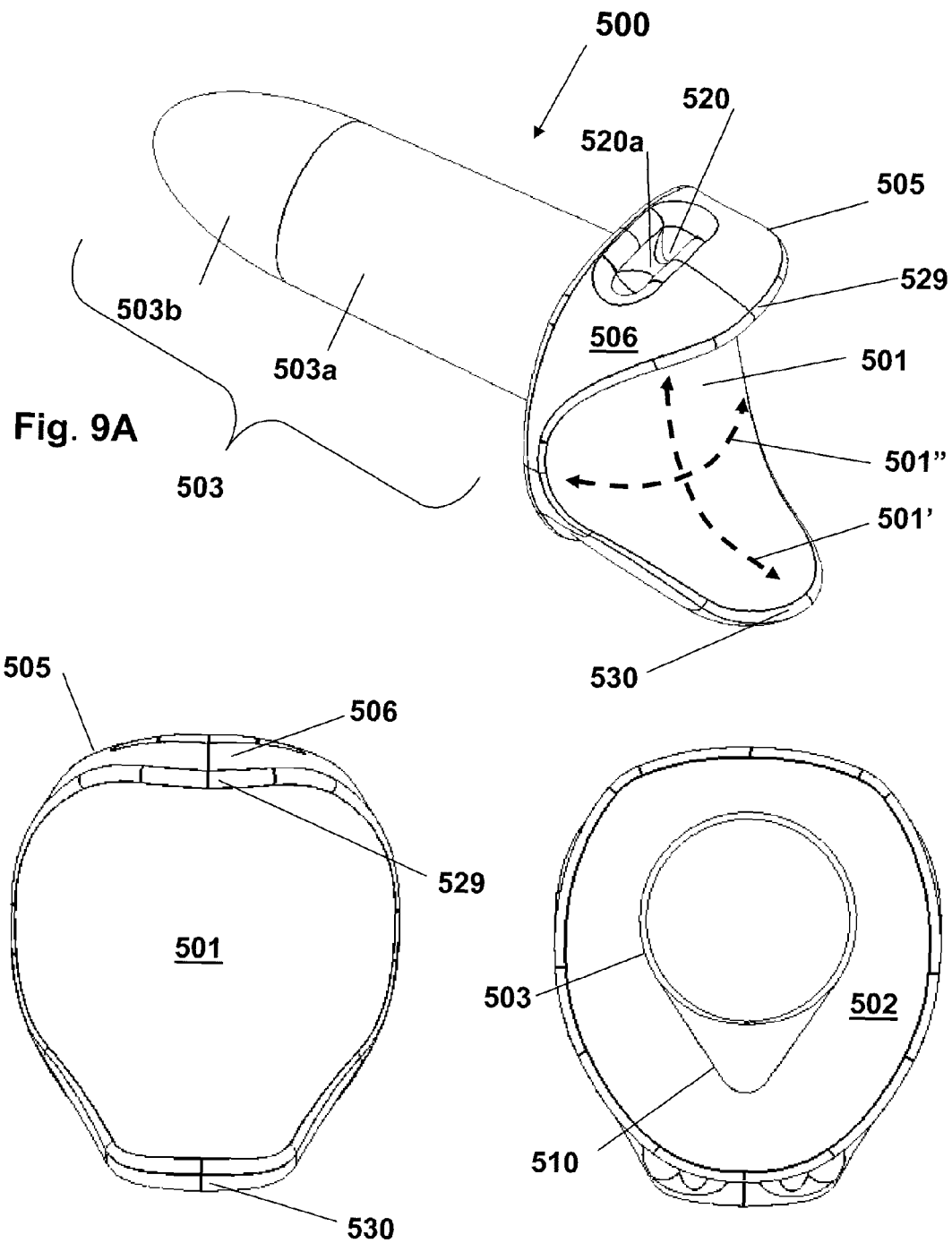

DEVICES, IMPLEMENTS AND METHODS FOR THE TREATMENT OF A MULTI-AXIS JOINT

CROSS-REFERENCE TO RELATED APPLICATIONS

The present application claims priority to Provisional Patent Application No. 61/347,517, filed on May 24, 2010 and to Provisional Patent Application No. 61/390,420, filed on Oct. 6, 2010, both of which are entitled DEVICES, IMPLEMENTS AND METHODS FOR TREATMENT OF A MULTI-AXIS JOINT; those applications being incorporated herein, by reference, in their entireties.

FIELD OF INVENTION

The invention relates to the treatment of diseased, multi-axis joints, and more particularly, to devices, implements and methods useful for the surgical treatment of arthritic, multi-axis joints for the early reestablishment of adequate range of motion, reduction or elimination of pain, recovery of strength and stabilization of the joint. The invention is particularly useful in connection with surgical treatment of the carpo-metacarpal joint and other similarly configured joints.

BACKGROUND OF THE INVENTION

The first carpo-metacarpal (i.e., 1CMC) joint, found at the base of the thumb, is complicated in that it does not have a single axis of rotation. Rather, the first metacarpal sits on the trapezium in a saddle-shaped geometry. This allows each of the bones in the first carpo-metacarpal joint to rotate about each other around axes of rotation oriented transversely to one another.

The 1CMC joint has a propensity to wear out and develop arthritis, causing pain at the base of the thumb and resulting in weakness of the gripping and pinching abilities of the hand. In patients with osteoarthritis, this condition is referred to as basal joint arthritis of the thumb. Conservative and medical treatments of the condition, including splints, NSAIDs and cortisone, are commonly used but are not always effective, leading to consideration of surgical solutions.

One surgical approach involves the removal of the trapezium, linking the first and second metacarpals at their bases with tendon graft and inserting a pad made of tendon graft or artificial material to cushion the space left by the now absent trapezium.

Other surgical approaches include the use of a prosthetic device to substitute one half or all of the 1CMC joint. Examples of these are described in U.S. Pat. No. 5,645,605 to Klawitter, International Publication WO2010/033691 also to Klawitter, U.S. Pat. No. 7,182,787 to Hassler and U.S. Pat. No. 7,641,696 to Ogilvie.

It has been observed that known surgical techniques and devices to treat the arthritic 1CMC joint achieve one or more of early reestablishment of adequate range of motion, reduction or elimination of pain, recovery of strength and stabilization of the joint, but none achieves all of them to a satisfactory degree.

Additionally, accurate means for performing a wedge osteotomy in small bones, a particularly useful arthroplastic procedure for restoring pain free stability to a patient with basal joint arthritis of the thumb, are not currently available. Furthermore, a prosthetic device that can be used to emulate the result of a wedge osteotomy is currently unavailable for those cases when replacement of a damaged articular surface is indicated.

What is needed is a system, apparatus and methods that provide a surgeon with surgical options and the corresponding devices to treat a diseased joint and to overcome the limitations of the heretofore-known devices.

SUMMARY OF THE INVENTION

It is, accordingly, an object of this invention to provide the surgeon with surgical options and the corresponding devices to treat the diseased joint and to overcome the limitations of the heretofore-known devices. In one particular embodiment of the invention, a wedge osteotomy system is provided for performing arthroplasty of the first carpo-metacarpal joint. In another particular embodiment a prosthesis that emulates the post-osteotomy geometry is provided to substitute the native proximal articular surface of the first metacarpal when so indicated. In a further embodiment of the invention, the devices are provided as part of a set that includes different size prostheses, to accommodate varied patient anatomies.

Although the invention is illustrated and described herein as embodied in Devices, Implements and Methods for the treatment of a Multi-Axis Joint, it is nevertheless not intended to be limited to only the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

BRIEF DESCRIPTION OF THE FIGURES

FIG. 1A is a diagrammatic view of the skeleton of the hand where the bones of the carpus and the first metacarpal are indicated.

FIG. 1B is an exploded view of the two bones that compose the first carpometacarpal joint indicating the two saddle-shaped articular surfaces of the bones.

FIGS. 4A-4B are side elevational views of the use of the cutting guide of FIGS. 3A-3B.

FIG. 9A is a perspective plan view from the dorsal side of a prosthesis according to one particular embodiment of the instant invention.

FIG. 9B is a front elevational view of the prosthesis of FIG. 9A

FIG. 9C is a rear elevational view of the prosthesis of FIG. 9A

DETAILED DESCRIPTION OF THE PREFERRED EMBODIMENTS

Figure 2:
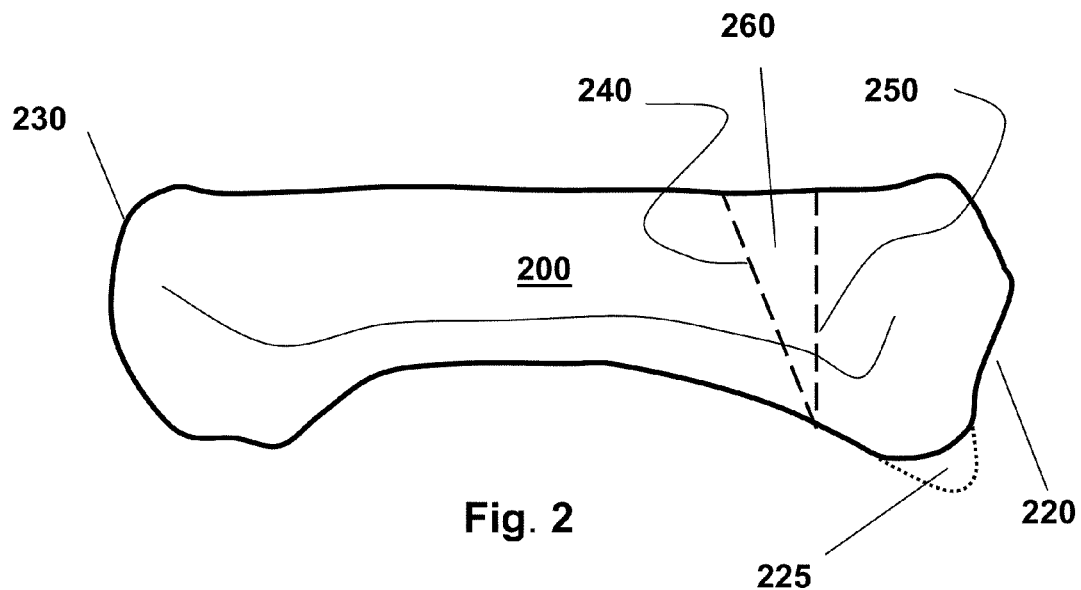
FIG. 2 is a side view of a first metacarpal bone, wherein the desired cutting lines for a wedge osteotomy are indicated.
Figures 3A, 3B:
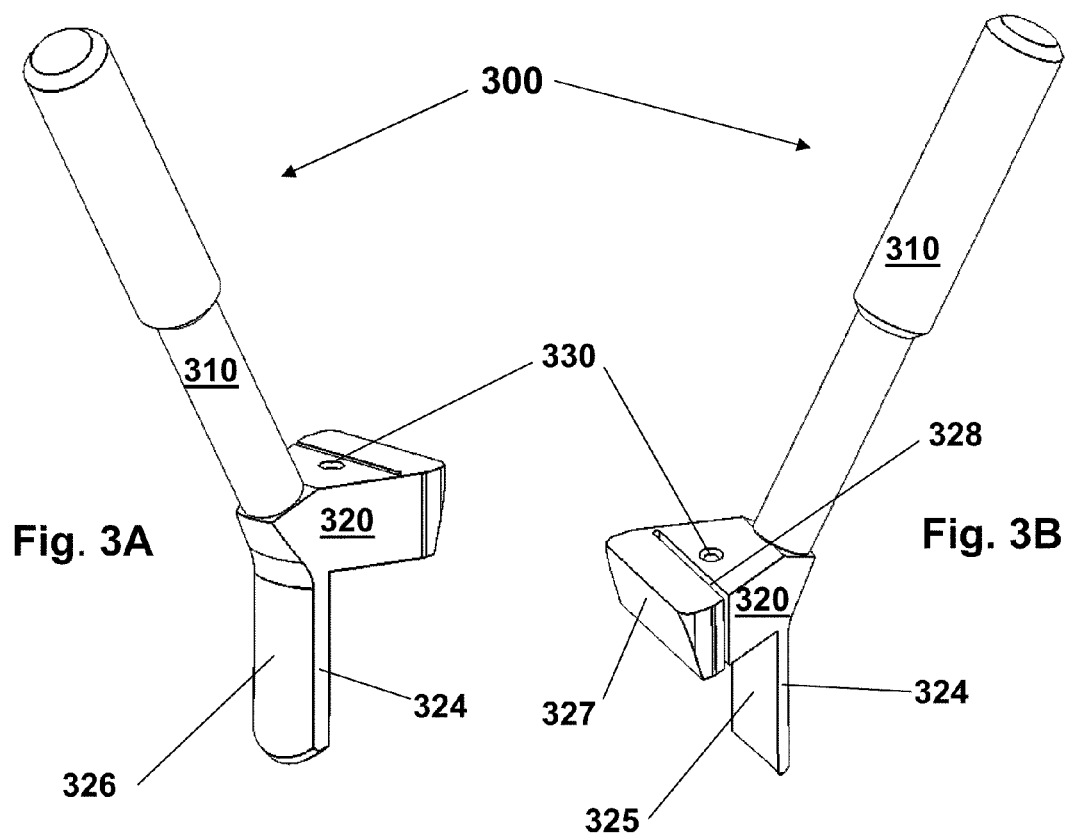
FIGS. 3A-3B are perspective views of a cutting guide in accordance with one particular embodiment of the instant invention.

A system, devices and methods for performing small bone arthroplasty are provided. In one particular embodiment of the invention, a cutting guide system for performing an osteotomy is provided, which uses the articular surfaces of the articulating bones as a reference for installing one or more K-wires used to position a cutting guide block in order to perform an osteotomy. Further, in accordance with one particular embodiment of the invention, a pre-formed plate and fasteners are provided to lever a resected bone portion into a desired position relative to another bone portion and, subsequently, to stabilize the bone portions to allow healing. For purposes of illustration only, the cutting guide system and method will be described in connection with the performance of a wedge osteotomy of the first metacarpal. Furthermore, when so indicated, in another particular embodiment of the invention a prosthesis may be provided to replace a damaged proximal articular surface of an articulating bone (a first metacarpal in the present example) with an artificial articular surface that emulates the post-osteotomy geometry, while harmonizing with the articular surface of the trapezium.

Referring more particularly to FIG. 1A, there is shown a skeletal representation of the human hand and, in particular, the bones of the carpus and the 1CMC joint; the trapezium 100, the trapezoid 101, the capitate 102, the scaphoid 103, the lunate 104, the triquetral 105, the pisiform 106, the hamate 107 and the first metacarpal 200. At their interface the first metacarpal 200 and trapezium 100 form the 1CMC joint at the base of the thumb.

Referring now to FIG. 1B, there is shown an exploded view of a 1CMC joint, formed from the interaction between the first metacarpal 200 and the trapezium 100, from which can be seen the saddle-shaped characteristics of the articular surfaces 220, 120 of the first metacarpal 200 and the trapezium 100, respectively. Such saddle-shaped articular surfaces 120, 220, are inherent in joints having more than one axis of rotation.

Referring now to FIG. 2, there is shown a first metacarpal (e.g. "1MC") bone 200 having a distal head portion 230 and a proximal articular surface 220 representing the typical profile of the 1MC bone in an arthritic patient. A portion 225 (shown dotted) represents the part of the 1MC bone of a healthy patient that has been eroded away as a consequence of the disease, causing loss of stability of the joint. Additionally shown are the intended proximal 250 and distal 240 cutting lines defining a wedge 260 to be removed from the 1MC as a step of the osteotomy to be performed.

A cutting guide 300 for performing small bone osteotomy in accordance with one particular embodiment of the invention will now be described in connection with FIGS. 1B, 2 and 3A-3B. More particularly, the cutting guide 300 includes a body portion 320 and a removable handle 310. The body portion 320 defines volarly projecting surfaces for aligning the cutting guide 300 at a desired angle and position relative to the 1MC for making a first intended distal cut along angled line 240 angled relative to the longitudinal axis of the 1MC. More particularly, the divider piece 324 of the guide 300 is placed into the joint between the 1MC 200 and trapezium 100 having its aligning surface 325 abutting the proximal articular surface 220 of the 1MC and its opposite surface 326 abutting the distal articular surface 120 of the trapezium. One or both surfaces 325, 326 can be contoured to the anatomy of the bone surface against which it will be placed, if desired, or, alternately, can be flat, planar surfaces. These surfaces 325, 326 align the saw guide at a desired, relative cutting angle and position. Furthermore, body portion 320 includes an angled plane surface 327, adapted to align a cutting blade along the angled line 240, and a vertical slot 328, adapted to align a cutting blade along cutting line 250, substantially perpendicular the longitudinal axis of the 1MC. In one particularly preferred embodiment of the invention, the angle of the angled plane surface 327 relative to a plane through the divider piece is 20 degrees +/−2 degrees. Additionally, body portion 320 includes at least one K-wire hole 330 configured to receive a K-wire therethrough, to provide stability for the cutting guide 300 while cuts are being made along the lines 240 and 250. The handle 310 can removably engage the body portion 320, for example, using a threaded shaft on the proximal end of the handle 310 that matingly engages a threaded bore of the body portion 320, or vice-versa.

A method of using the cutting guide 300 will now be described in connection with FIGS. 3A-4B. More particularly, once the divider piece 324 is inserted in a dorsal to palmar direction into the 1CMC joint with its aligning surface 325 abutting the proximal articular surface 220 of the 1MC, a first K-wire 335 is drilled into the 1MC 200, also in a dorsal to palmar direction, via the K-wire hole 330 of body portion 320 of the saw guide 300. The K-wire 335 provides stability for the saw guide 300 and, if desired, the resulting bore in the 1MC 200 may be used for future screws that may need to be placed at that location.

Once the body portion 320 is stabilized by the K-wire 335, an oscillating saw 350 may be used to make a first distal cut 240' in the 1MC 200, by aligning the oscillating saw blade with angled plane surface 327. Subsequently, the K-wire 335 may be bent into position 335', (shown in dotted line in FIG. 4A) to provide clearance for the blade 350a of the oscillating saw 350 to be inserted into the vertical slot 328 to make the proximal cut 250', substantially perpendicular to the longitudinal axis of 1MC. As can be seen more particularly from FIG. 4B, after completing the distal cut 240' and the proximal cut 250', a wedge shaped portion of 260 of the 1MC bone will remain and, as will be described more particularly below, should be removed as one further osteotomy step in carrying out the arthroplasty.

If desired, as part of a system for the arthroplasty, a plurality of cutting guide body portions 320 may be provided, each having a plane surface 327 at a different angle from the rest, for making distal angled cuts 240' to accommodate different patient anatomies. In another embodiment the cutting guide body portion 320 may include a mechanism (i.e., an angle adjustment screw) for adjusting the angle of plane surface 327 relative to the divider piece 324, prior to making the distal cut.

Referring now to FIGS. 5A-5F, in accordance with one particular embodiment of the present invention, a formable or pre-formed plate 400 is provided, which includes at least one hole 440 for receiving a bone fastener. The plate 400 is made of titanium or other bio-compatible metal or rigid material. In the particular embodiment shown in FIG. 5A, a pre-formed plate 400 includes a body portion 410, a Y-shaped head portion 430 oriented transverse to, and angled relative to, the body portion 410. In other words, in the present particular embodiment of FIGS. 5A-5E, the body portion 410 is not located in the same plane as the head portion 430. Plate 400 further includes a neck portion 420 joining the body portion 410 and the head portion 430. Head portion 430 includes at least one hole 440 which may be threaded and intended to receive a bone fastener (i.e. screw or peg 490 of FIG. 6B) which may have a threaded (locking) or un-threaded head and at least one substantially smaller, non-threaded contouring hole 460 for receiving a contouring tool (not shown). Body portion 410 is elongated and includes at least one hole 440 and at least one contouring hole 460 for receiving, respectively, a bone fastener and a contouring tool, as previously described. Additionally, in one particular embodiment of the invention, the body portion 410 includes at least one unthreaded slot 450 that permits adjustment of the position of the plate after a fastener has been inserted through the slot and into an underlying bone.

Figure 5A:
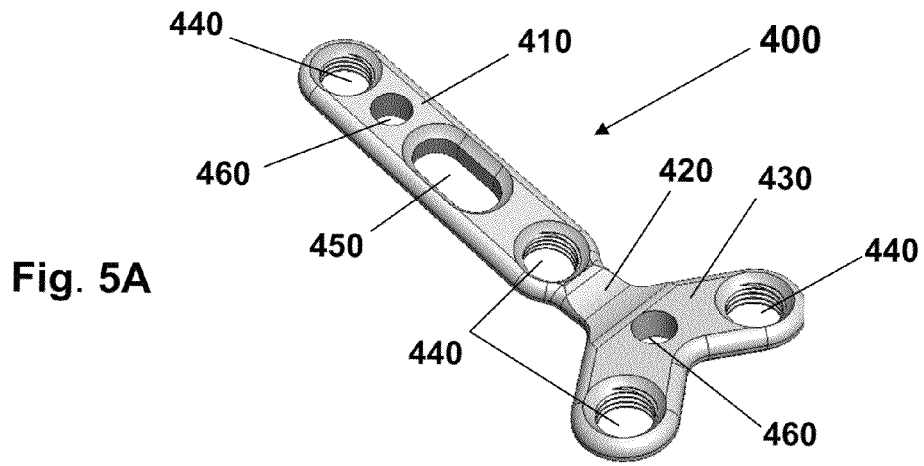
FIGS. 5A-5D are perspective, plan from above, plan from below and lateral elevational views of a plate in accordance with another particular embodiment of the instant invention.
Figure 5B:
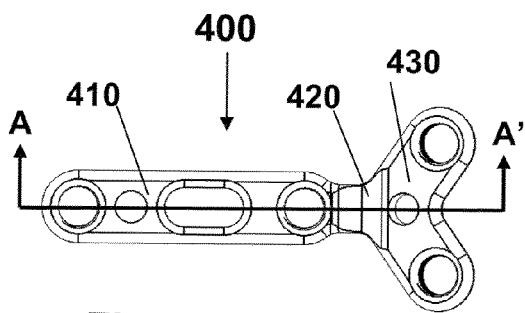
Figure 5C:
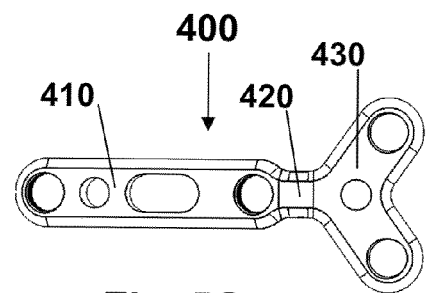
Figure 5D:
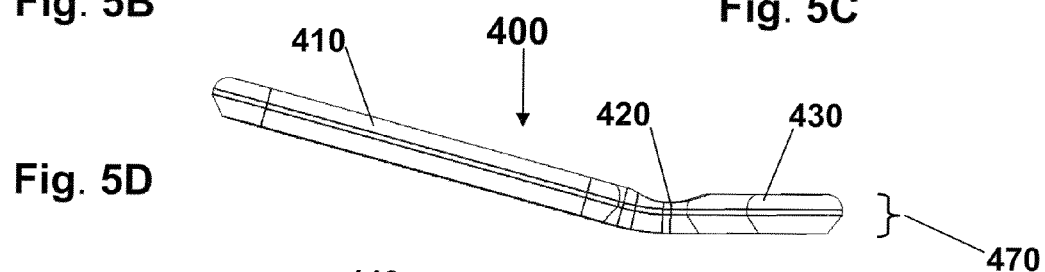
Figure 5E:
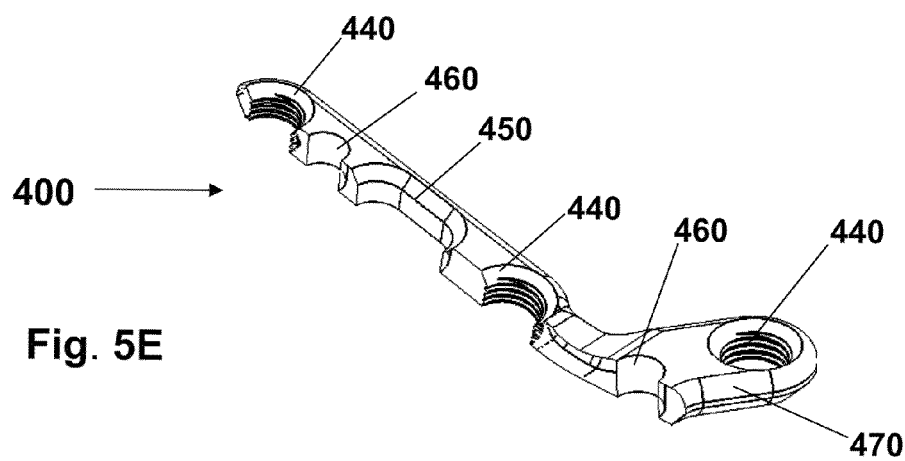
FIG. 5E is a perspective cross sectional view of the plate of FIG. 5B corresponding to cross section A-A'.
Figure 5F:
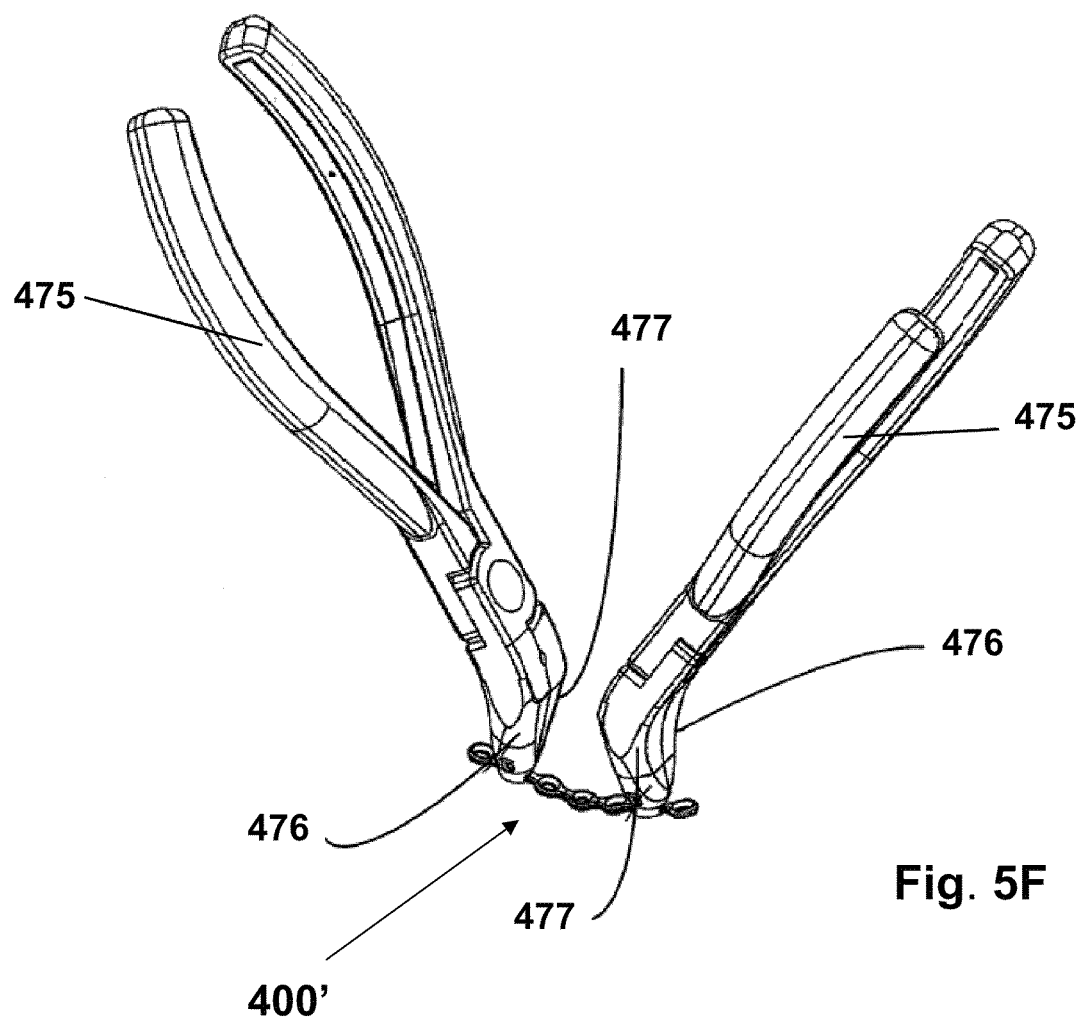
FIG. 5F is a perspective view of a plate being contoured by contouring pliers, according to a further particular embodiment of the instant invention.

In one particular embodiment of the invention shown in FIGS. 5D-5F, the entire perimetral edge 470 of the plate 400 has a convex shape adapted to be securely held by one or more contouring pliers 475 that can apply bending and/or torqueing forces to the plate 400, 400' for bending it into a desired configuration before or after the plate 400, 400' has been affixed to one or more bone portions.

Figure 6A:
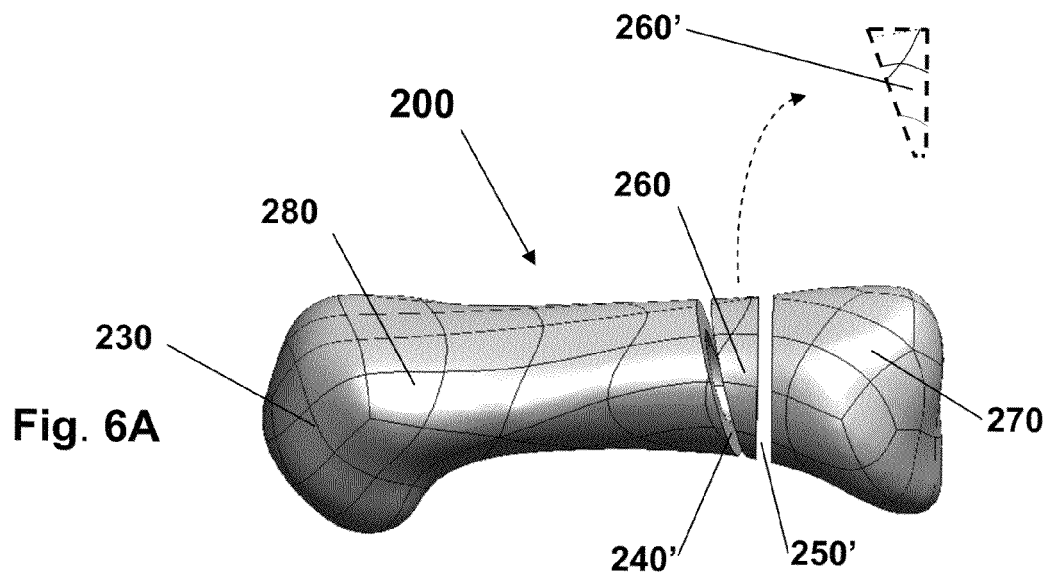
FIGS. 6A-6C are side elevational views of a first metacarpal bone subjected to a wedge osteotomy according to a particular embodiment of the invention.

Referring now to FIG. 6A, there is shown a lateral view of a 1MC bone 200 after cuts 240' and 250' of the above-described osteotomy have been made, thus creating three bone fragments: 1) a proximal bone fragment 270 including the proximal articular surface 220; 2) a distal bone fragment 280 including distal head 230; and 3) a wedge-shaped bone fragment 260. Wedge-shaped bone fragment 260 is removed and discarded (see 260') to allow for further execution of the arthroplasty.

As previously described above, in one particular embodiment of the invention, the pre-formed plate 400 includes a body portion 410 angled relative to a head portion 430. Optionally, the plate portion 400 may be manufactured and/or provided as a flat plate, and contoured preoperatively to have the desired angle using contouring tools or contouring pliers as will be further explained below.

Figure 6B:
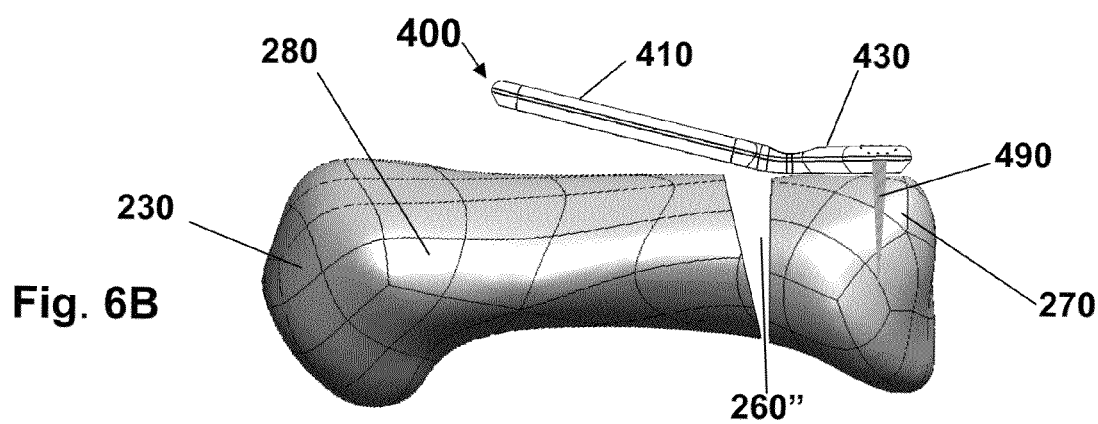
Figure 6C:
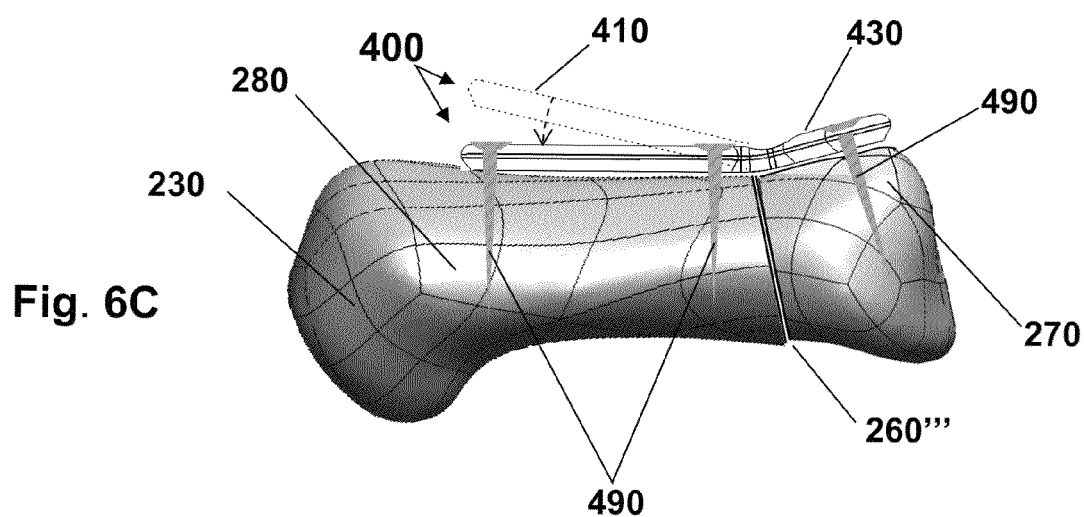

As further shown in FIG. 6B, head portion 430 can be affixed to the proximal bone fragment 270, using bone fasteners 490. Once so affixed, as further shown in FIG. 6C, the angled body portion 410 can be used as a handle to manipulate the position of bone fragment 270 relative to bone fragment 280 and, once in the desired position, as a lever to pivot down the proximal bone fragment 270, closing gap 260", into a desired abutting position relative to the distal bone fragment 280. Once gap 260" has been reduced to form contacting surfaces 260''' conducive to bone healing, plate body portion 410 can, in turn, be secured to bone fragment 280 with bone fasteners 490.

As may be required, prior to securing bone fragment 280 to the plate 400 with permanent bone fasteners 490, the instant invention provides for adjustment of the relative position of bone fragments 280, 270 by using a temporary fastener placed into bone fragment 280 through slot 450, to permit longitudinal adjustment of the plate 400 along the bone portion 280. Rotational adjustment of the bone fragments can be also achieved before or after placing permanent bone fasteners 490 by bending and/or torqueing the plate with the aid of contouring tools (i.e. bending irons, not shown) inserted into one or more contouring holes 460 in the head portion 430 and body portion 410 of plate 400 and, subsequently levering the tools. The contouring tool may be configured to penetrate to the depth of the contouring holes 460 to permit plate deformation only or, alternatively, may be configured to also extend, i.e., penetrate, into the underlying bone fragment, thus permitting plate deformation coupled with movement of the underlying bone fragment. Furthermore, the plate 400' may be also be contoured by using contouring pliers 475 (see FIG. 5F) with jaws 476, 477 adapted to securely engage the convex profile 470 along any location on the periphery of the plate 400, as is described more particularly in U.S. Patent Application Publication No. 2009/281543, published on Nov. 12, 2009, that publication being incorporated herein, by reference, in its entirety.

It is known that, when performing an arthroplasty of a CMC joint, it is often necessary to remove osteophytes from the distal articular surface of a carpal bone. In the case of the 1CMC joint, the relevant carpal bone is the trapezium. Typically, access to the osteophyte is limited and, if the osteophyte is large, it is difficult and time consuming to remove with a manual rongeur or osteotome, sometimes taking up to one third of the total surgical time. Further, manual removal of the osteophyte requires a high degree of surgical experience and "artistry" in order to avoid damage to the articular surface. Conversely, using a powered device for removal, such as an unprotected rotating burr, can lead to inadvertent removal of good bone and permanent damage to the articular surface.

It is, therefore, advantageous to provide tools and methods for a more rapid, precise and safe removal of the osteophyte(s). Such a combination of tools is provided by a thin saddle-shaped shield (not shown) in conjunction with a powered diamond tip burr to accurately remove the osteophyte while, simultaneously, protecting the articular surface and surrounding soft tissue.

The shield is inserted into the joint and used to protect good bone and soft tissue while the osteophyte is removed and the trapezium is shaped with the powered burr.

Although desirable, a wedge osteotomy that preserves the proximal articular surface of the metacarpal 220 as described above in reference to the arthroplasty of the 1CMC, may be found, during surgery, to not be the indicated procedure. Therefore, it is advantageous, as an alternative to such wedge osteotomy, to provide in the surgical kit a set of prostheses that can be implanted to emulate what would be the post-osteotomy result of the above referred arthroplasty of the 1CMC.

Figure 7A:
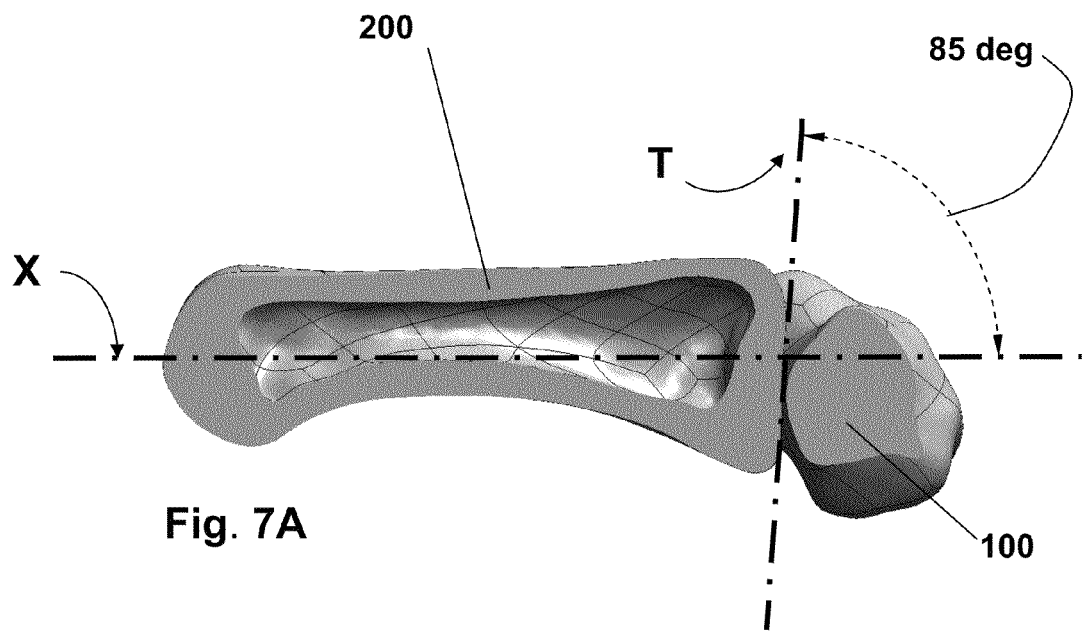
FIGS. 7A-7B are side sectional views of a first metacarpal bone and a trapezium bone illustrating the geometrical relationship between the bones before and after the performance of a wedge osteotomy according to a particular embodiment of the invention.

Referring now to FIG. 7A therein is shown a section in the dorsal-palmar plane through a 1MC bone 200, the corresponding trapezium 100 and the 1CMC joint. As can be noted, a plane T tangent to the dorsal and palmar lips of the preosteotomy 1MC portion of the 1CMC joint is inclined at an angle of approximately 85 degrees relative to a longitudinal axis X of the 1MC bone.

Figure 7B:
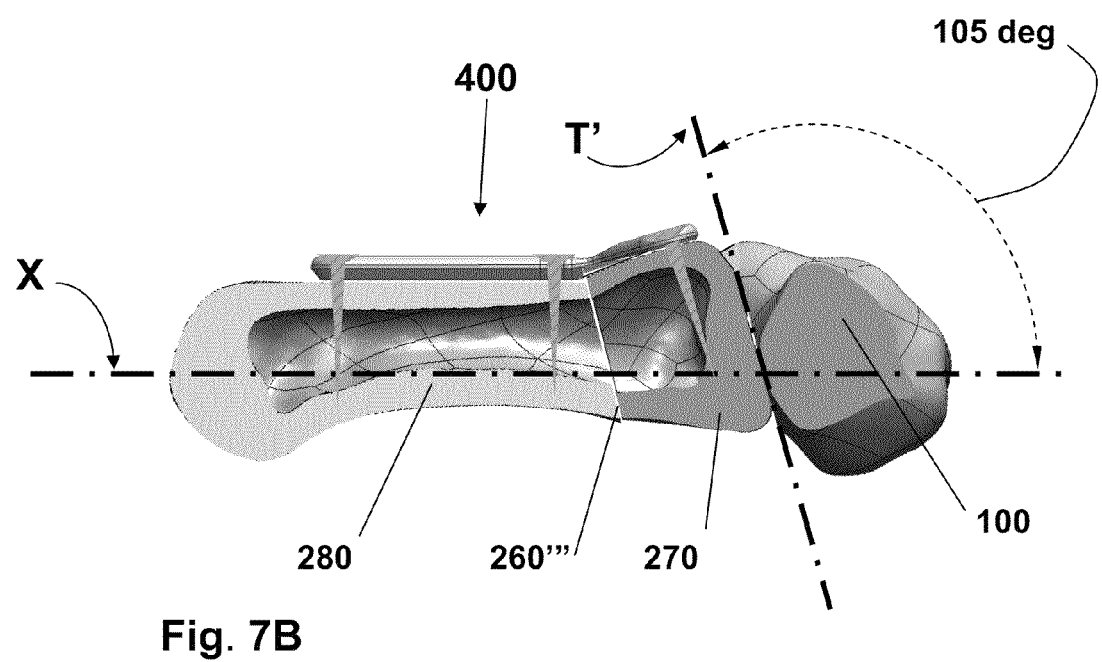

As shown in FIG. 7B, after wedge osteotomy, the palmar lip of the proximal articular surface protrudes significantly beyond the dorsal lip such that a plane T' tangent to both lips is inclined at an angle of approximately 105 degrees relative to longitudinal axis X. This rearranged geometry changes the tendon vector and is beneficial to the stability to the post-osteotomy 1CMC joint.

Figure 8:
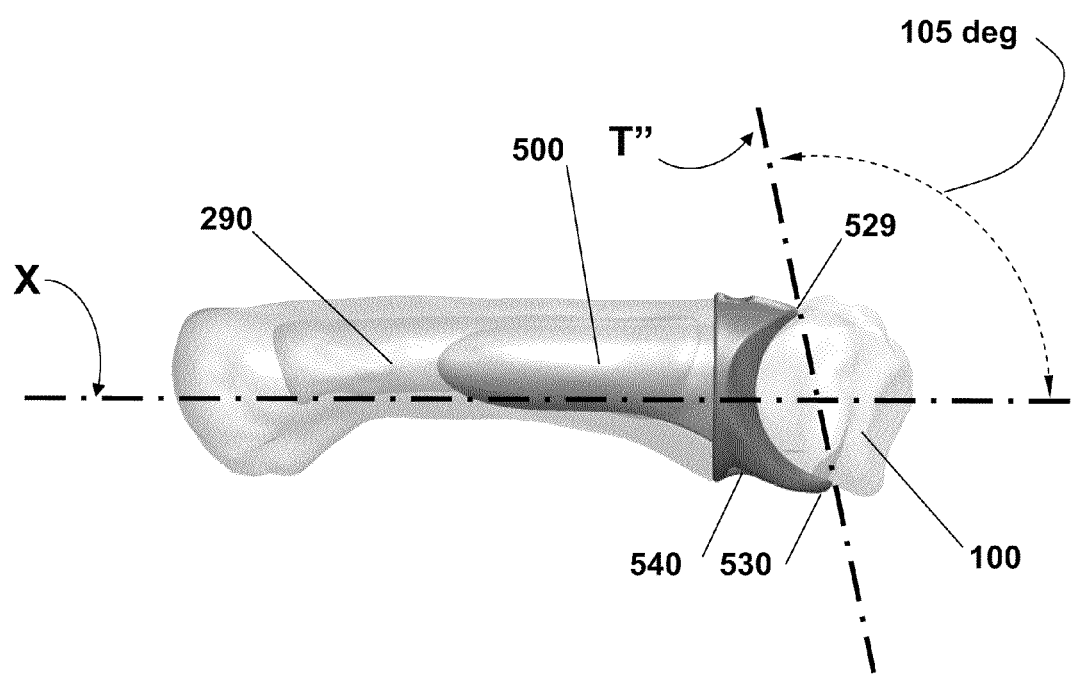
FIG. 8 is a side view of a first metacarpal bone having a prosthesis in accordance with one particular embodiment of the invention and a trapezium bone illustrating the geometrical relationship between the bones that emulates the result of a wedge osteotomy.

It is desirable that, in a similar manner, a prosthesis intended to substitute the native proximal articular surface of the 1MC emulate the post-osteotomy geometry illustrated above in FIG. 7B. Such similar geometry is shown in FIG. 8, with reference to a prosthesis 500 implanted into a 1MC bone 290, wherein a plane T" tangent to the dorsal and palmar lips of the prosthesis 500 is inclined at an angle of approximately 105 degrees relative to longitudinal axis X. Compare FIG. 8 with FIG. 7B.

Consequently, according to a further advantageous embodiment of the instant invention, a set of prostheses of different sizes is provided to accommodate a substitution for varying anatomies of the native articular surface of a 1MC bone that include a palmar lip protruding significantly relative to the dorsal lip. This provides a desired post-arthroplasty geometry leading to increased stability and will prevent subluxation of the joint.

Figure 9D:
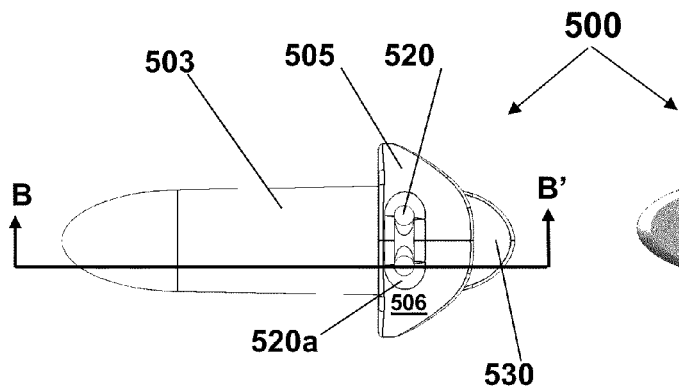
FIG. 9D is a top plan view of the dorsal side of the prosthesis of FIG. 9A
Figure 9E:
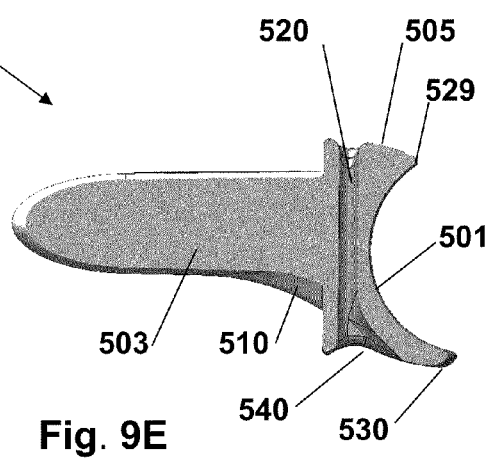
FIG. 9E is a cross-sectional view of the prosthesis of FIG. 9D in corresponding to cross section B-B'
Figure 9F:
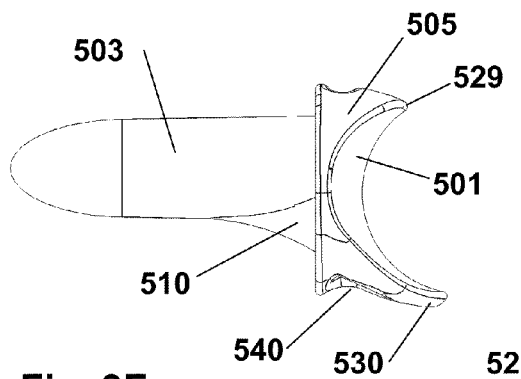
FIG. 9F is a side elevational view of the prosthesis of FIG. 9A
Figure 9G:
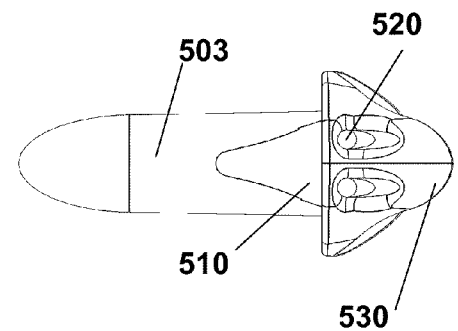
FIG. 9G is a bottom plan view of the palmar side of the prosthesis of FIG. 9A.

Referring now to FIG. 9A, there is shown one particular embodiment of a prosthesis 500, in accordance with the present invention. Prosthesis 500 includes a distal stem portion 503 adapted for insertion into the medullary cavity of a first bone and a proximal head portion 505 adapted to articulate with a second bone forming a joint with the first bone. Stem portion 503 includes a proximal frusto-conical portion 503a and a distal rounded or bullet shaped portion 503b. The head portion 505 includes a saddle shaped articular surface 501 that is circularly concave 501' in the dorsal-palmar plane and circularly convex 501" in the lateral-medial plane.

Further referring now to FIGS. 9A and 9B, head portion 505 of prosthesis 500 also includes a generally ovoidal (i.e. egg-shaped), peripheral surface of continuous curvature 506 surrounding the totality of the head portion, with the pole of the ovoid having less curvature oriented towards the dorsal side and with an edge being defined at the interface of the peripheral surface 506 and the articular surface 501. This edge further defines a dorsal lip 529 at the dorsal pole of the head portion and a palmar (or volar) lip 530 at the opposite volar pole of the head portion. As can be better appreciated in FIG. 9A the palmar lip 530 protrudes significantly relative to dorsal lip 529.

Referring now to FIGS. 9A-9C, the head portion 505 also includes a flat portion 502 opposite the articular surface 501. Flat portion 502 is adapted to abut against the edge of a bone that has been resected as part of an osteotomy procedure. Emerging from flat portion 502 on the palmer side of the prosthesis 500 and blending in a distal direction with stem portion 503, the prosthesis 500 includes a keel portion 510, configured to impede the rotation of stem portion 503 during and after insertion into the medullary cavity of a bone.

Referring now to FIGS. 9A-9H, in one particular embodiment of the instant invention, the head portion 505 also includes a plurality of suture holes 520 which, beginning and ending within peripheral surface 506, traverse the head portion 505 vertically in a dorsal to palmar direction and include, on the dorsal side, a recess 520a adapted to accommodate the knot of a suture. The suture holes 520 exit on the palmar side of surface 506 inside a transverse groove 540. As will be further described below, this transverse groove 540 is adapted to allow the passage of the Flexor Carpi Radialis ("FCR") tendon under the prosthesis 500.

Additionally, as described above, should a prosthesis be required, it is advantageous to have access to a set of prostheses of different sizes to accommodate varying anatomies. Consequentially, in one particular embodiment of the instant invention, at least three sizes of prosthesis 500 are provided, ranging from the largest to the smallest that have been selected by anatomical observation. In one embodiment, the approximate dimensions of the largest prosthesis are: head portion 505, height and width (0.61 in×0.60 in); stem portion 503, length and major diameter (0.98 in×0.33 in); saddle-shape articular surface 501, convex radius of curvature and concave radius of curvature (0.47 in×0.33 in). In this same embodiment, the approximate sizes of the smallest prosthesis are: head portion 505 height and width (0.48 in×0.39 in); stem portion 503 length and major diameter (0.71 in×0.23 in); saddle-shape articular surface 501, convex radius of curvature and concave radius of curvature (0.3 in×0.26 in). Prostheses of intermediate sizes may be dimensioned by interpolation of the largest and smallest dimensions.

The inclusion of only three prostheses in a set is not meant to be limiting, as the number of different sizes of prosthesis to be provided in the set can vary. However, it is preferred that a range of three to five prostheses of varying sizes be provided in a set, as desired. However, a greater number or smaller number of prostheses can be provided in a set, without departing from the scope of the present invention. Similarly, the dimensions referred to above are exemplary and are not intended to be limiting in any way.

A set of trial prostheses (not shown), generally matching the dimensions of the prosthesis 500, may also be provided if desired. These trial prostheses can be used to help in the selection of the final prosthesis to be installed. Additional instruments in the form of rasps, cutting guides, punches and impactors (not shown) may also be provided as part of the surgical set, if desired.

Figure 9H:
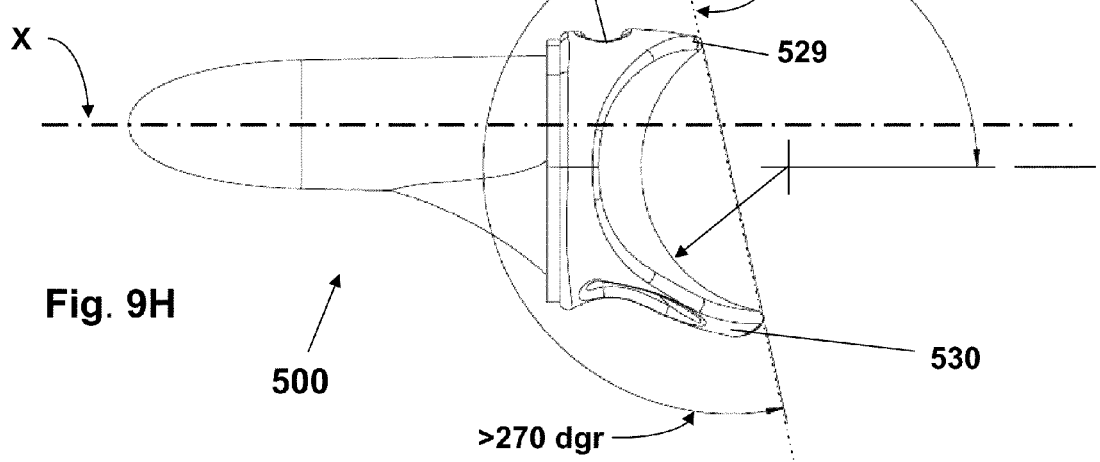
FIG. 9H is a side elevational view of the prosthesis of FIG. 9A indicating the geometrical relationship between the dorsal lip and the palmar lip.

As described hereinabove, the provided prostheses advantageously include a palmar lip that protrudes significantly relative to the dorsal lip to provide the desired post-arthroplasty geometry leading to increased stability and prevention of subluxation of the joint. Referring more particularly to FIG. 9H, there is shown one particular example of the extent to which it is desirable that the palmar lip protrude beyond the dorsal lip. Considering a line T'" tangent to the most proximal point on the dorsal lip that is also tangent to the most proximal point of the palmar lip, such line will be inclined at an angle of more than 270 degrees relative to the longitudinal axis X of the prosthesis, and preferably at an angle ranging between 283 degrees and 287 degrees. However, the invention is not intended to be limited to only these dimensions, as other dimensions and angles can be effective and/or used without departing from the scope and spirit of the instant invention.

Figure 10A:
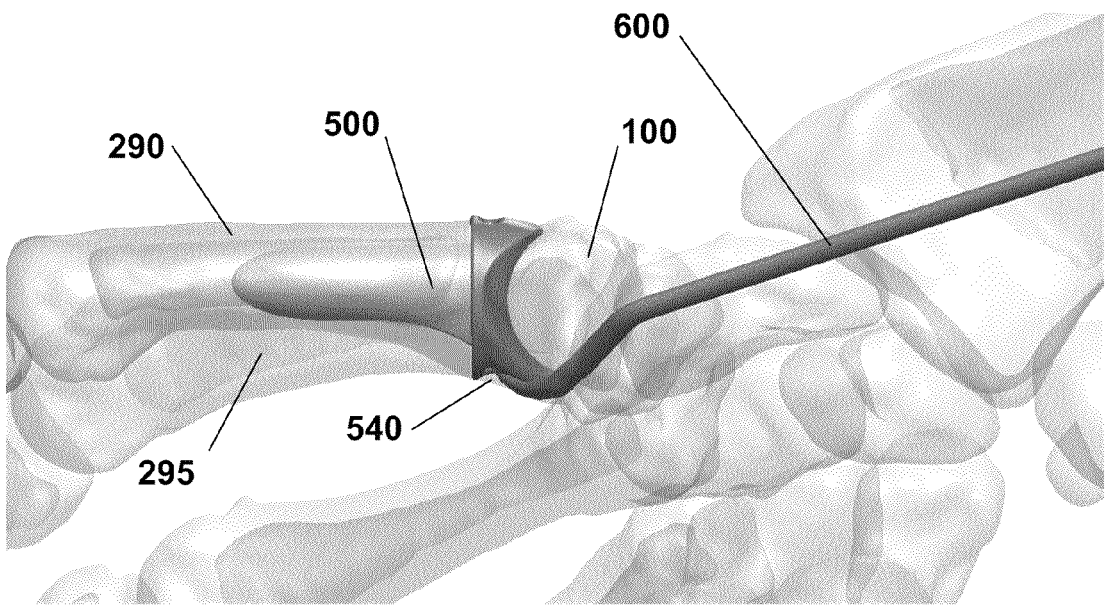
FIGS. 10A-10B are, respectively, side elevational and top plan views of the prosthesis of FIG. 9A installed in a first metacarpal bone and its relationship to the trapezium bone and the flexor carpis radialis tendon.
Figure 10B:
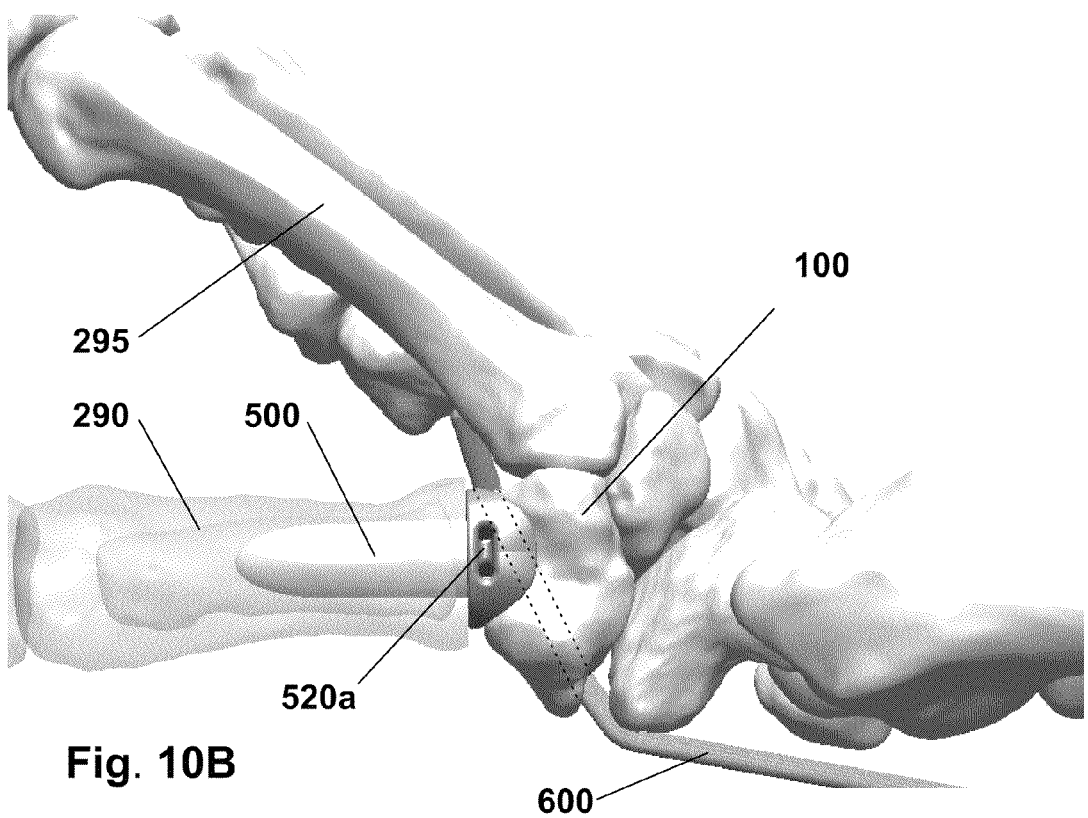

Referring now to FIGS. 10A-10B, as described above, the prosthesis 500 is provided with suture holes 520 and a transverse groove 540 to allow the unimpeded passage of the FCR tendon 600 under the prosthesis 500. The FCR tendon 600 passes under the trapezium 100 to insert itself into the second metacarpal bone. FIGS. 10A-10B show, respectively, a lateral and dorsal view of the FCR tendon 600 passing under the trapezium 100 and transversely under the FCR groove 540 to finally attach itself to second metacarpal bone 295. In order to maintain this position while the arthroplaticized joint heals, it has been found to be advantageous to have the FCR tendon 600 sutured temporarily within the groove 540. This can be achieved by using absorbable sutures through the FCR tendon 600, passing the sutures through the suture holes 520 provided, and tying the sutures at the notch 520a in the dorsal side of the peripheral surface 506 of the prosthesis 500.

In one particular preferred embodiment of the invention, the prostheses 500 are made of highly polished cobalt chromium and may be coated with titanium plasma spray coating on any or all of the flat surface 502, the stem 503 and the keel 510. The trial prostheses, if provided, may be made of aluminum or other bio-compatible material.

A method will now be described for installing prosthesis 500 as a substitute for the proximal articular surface of the 1MC bone. A surgeon will expose the 1CMC joint with an incision centered over the joint, along the course of the extensor pollicis brevis ("EBP") tendon and releases the tendon from proximal to distal and retracts it ulnarly. The abductor pollicis longus ("APL") tendon is then partially released, and the joint capsule is released circumferentially to allow access to the 1CMC joint. To gain further access to the joint space, the base of the first metacarpal is resected just below the articular surface and the volar aspect of the 1CMC capsule is released to allow identification and removal of osteophytes on the trapezium. The medullary canal is broached with a rasp until cortical bone is contacted circumferentially and the proximal end of the 1MC is resected perpendicularly using a guide attached to the rasp, if provided. A punch is used to create a cavity for receiving the keel 510 of a prosthesis 500. Trial prostheses, if provided, may be installed to test the reduction and help to select the size of the final prosthesis 500. If desired, a locking stitch may be performed through the FCR, using absorbable sutures, leaving even lengths of suture at both ends. These two free ends of the sutures are passed through the two suture holes 520 of the prosthesis 500 in a palmar to volar direction and kept taut. The prosthesis 500 is installed by inserting the stem 503 into the prepared medullary canal and impacting it in place and the free ends of the suture are secured on the dorsal side of the prosthesis 500 with a knot in the provided recess 520a. After installation, proper kinematics and stability are tested by manipulating the joint through its full range of motion and confirmed fluoroscopically. Finally, soft tissues are repaired as needed before the incision is closed.

Although the foregoing examples have been given in connection with a carpo-metacarpal joint, it should be understood that this is not meant to be limiting, as the guides, instruments, plates and prostheses described herein can be adapted for use in different joints without departing from the scope of the present invention. For example, the implements described herein can be made in accordance with the description herein, but of different size or scale, so as to treat instability or dislocations of other multi-axis hinged joints, as desired. Thus, although the preferred embodiments of the invention are illustrated and described herein, various modifications and structural changes may be made therein without departing from the spirit of the invention and within the scope and range of equivalents of the claims.

What is claimed is:

1. A prosthesis for a first bone of a joint, comprising:
   a head portion adapted to articulate with a second bone of the joint, said head portion including an articular surface emulating a native post-osteotomy articular surface of the first bone, said articular surface including a saddle shaped articular surface that is circularly concave in a dorsal-palmar plane and circularly convex in a lateral-medial plane;
   the head portion including a dorsal lip and a palmar lip, the palmar lip protruding beyond the dorsal lip such that a line tangent to a most proximal point on the dorsal lip that is also tangent to a most proximal point on the palmar lip will be inclined at an angle of more than 270 degrees relative to a longitudinal axis through the prosthesis;
   a stem portion adapted for insertion into the medullary cavity of the first bone; and
   a keel portion extending from a palmar side of said stem.

2. The prosthesis of claim 1, wherein the stem portion includes a proximal frusto-conical portion and a rounded distal portion.

3. The prosthesis of claim 2, wherein the keel is configured to impede the rotation of stem portion in a medullary canal.

4. The prosthesis of claim 1, wherein the head portion includes a generally ovoidal, peripheral surface of continuous curvature surrounding the head portion.

5. The prosthesis of claim 1, wherein the head portion includes a transverse groove configured to allow the passage of the Flexor Carpi Radialis ("FCR") tendon.

6. The prosthesis of claim 1, wherein the head portion includes at least one suture hole traversing the head portion in a dorsal to palmar direction.

7. The prosthesis of claim 6, wherein the at least one suture hole is disposed in a transverse groove of the head portion.

8. A set of prostheses of different sizes to accommodate varying anatomies, each prosthesis of said set of prostheses being configured according to claim 1.

9. A method of installing a prosthesis, comprising:
   exposing and resecting a first bone of a joint below an articular surface of the bone;
   providing the prosthesis of claim 1; and
   inserting the stem of the prosthesis into the medullary canal until a flat surface on the head portion abuts a surface of the resected first bone.

10. The method of claim 9, wherein the the stem portion further includes a keel configured to impede the rotation of stem portion in a medullary canal.

11. The method of claim 9, wherein at least one trial prosthesis is used to help select the size of a final prosthesis.

12. The method of claim 9, further including the steps of:
    before said inserting step, using a suture to place at least one locking stitch through the FCR tendon; and
    passing the free end of the suture through the at least one suture hole and keeping the suture taut; and
    after the inserting step, knotting the suture on the dorsal side of the prosthesis.

13. The method of claim 12, wherein the head portion of the prosthesis additionally includes a transverse groove, said transverse groove including at least one suture hole through which the suture is passed and knotted in the knotting step.

* * * * *